United States Patent [19]

Oren et al.

[11] Patent Number: 4,968,508

[45] Date of Patent: Nov. 6, 1990

[54] SUSTAINED RELEASE MATRIX

[75] Inventors: Peter L. Oren, Noblesville; Werner M. K. Seidler, Indianapolis, both of Ind.

[73] Assignee: Eli Lilly and Company, Indianapolis, Ind.

[21] Appl. No.: 300,457

[22] Filed: Jan. 19, 1989

Related U.S. Application Data

[63] Continuation of Ser. No. 136,628, Dec. 22, 1987, which is a continuation-in-part of Ser. No. 19,915, Feb. 27, 1987, abandoned.

[51] Int. Cl.$^5$ .......................... A61K 9/22; A61K 9/36
[52] U.S. Cl. ..................... 424/468; 424/469; 424/470; 424/473; 424/479; 424/480; 424/482
[58] Field of Search ............... 424/484, 465, 468, 470, 424/469, 480, 479, 482, 473

[56] References Cited

U.S. PATENT DOCUMENTS

| | | | |
|---|---|---|---|
| 3,065,143 | 4/1960 | Christenson et al. | 167/82 |
| 3,458,622 | 7/1969 | Hill | 424/19 |
| 4,252,786 | 2/1981 | Weiss et al. | 424/19 |
| 4,309,405 | 1/1982 | Gulley et al. | 424/21 |
| 4,389,393 | 6/1983 | Schor et al. | 424/19 |
| 4,520,009 | 5/1985 | Dunn | 424/78 |
| 4,521,401 | 6/1985 | Dunn | 424/19 |
| 4,521,402 | 6/1985 | Dunn | 424/19 |
| 4,522,804 | 6/1985 | Dunn | 424/19 |
| 4,800,084 | 1/1989 | Zerbe | 424/467 X |

FOREIGN PATENT DOCUMENTS

| | | |
|---|---|---|
| 129382 | 12/1984 | European Pat. Off. . |
| 142877 | 5/1985 | European Pat. Off. . |
| 2067072 | 7/1981 | United Kingdom . |

OTHER PUBLICATIONS

Remington's Pharmaceutical Sciences, Mack Publishing Company, 16th Edition (1980).
Chemical Abstracts 99:110763C.

*Primary Examiner*—Thurman K. Page
*Attorney, Agent, or Firm*—William B. Scanlon; Leroy Whitaker

[57] ABSTRACT

This invention provides a matrix composition for sustained drug delivery which is comprised of an active agent, a hydrophilic polymer and an enteric polymer. The enteric polymer is impermeable to gastric fluids and aids in retarding drug release in regions of low pH, thus allowing lower levels of hydrophilic polymer to be employed. At the pH range of intestinal fluids, this polymer will dissolve and thereby increase the permeability of the dosage form. This approach is useful in sustaining the release of numerous active agents whose solubility declines as the pH is increased, a characteristic of weakly basic drugs. By responding to changes in physiological pH, these sustained release dosage forms have acceptable performance, in spite of variability in the gastrointestinal transit times of the formulation.

5 Claims, No Drawings

SUSTAINED RELEASE MATRIX

CROSS-REFERENCE TO RELATED APPLICATIONS

This application is a continuation of application Ser. No. 07/136628, filed Dec. 22, 1987, which is a continuation-in-part of application Ser. No. 07/019,915, filed Feb. 27, 1987, now abandoned.

BACKGROUND OF THE INVENTION

Ideally, a sustained release dosage form should deliver the medicament at a constant rate throughout the gastrointestinal tract. With many of the delivery systems currently available, this expectation may not be realized since many drugs which are weakly acidic or basic exhibit solubility which varies in relation to pH. A decline in solubility in response to pH fluctuations within the body may result in a decreased release rate if the formulation does not respond with an appropriate change in its permeability characteristics.

The use of hydrophilic matrices to provide sustained drug release is known. Christenson et al. in U.S. Pat. No. 3,065,143 disclose the use of certain hydrophilic gums, including hydroxypropyl methylcelluloses, in the preparation of sustained release tablets. Hill in U.S. Pat. No. 3,458,622 describes the preparation of sustained release tablets using a combination of povidone and carbopol. Weiss et al. in U.S. Pat. No. 4,252,786 describe a controlled release tablet consisting of a core tablet which was identical to the tablet disclosed in Hill, that is, containing an active ingredient, povidone, and carbopol. A coating consisting of a hydrophobic and a hydrophilic polymer was employed to prevent the initial burst of drug release encountered with this tablet. Schor et al. in U.S. Pat. No. 4,389,393 describe sustained release therapeutic compositions based on high molecular weight hydroxypropyl methylcellulose. Guley et al. in U.S. Pat. No. 4,309,405 describe a sustained release pharmaceutical composition comprising a compressed core, a seal coating surrounding the core and a sugar coating surrounding the seal coated core wherein, a) the core consists of an active ingredient, at least one pharmaceutically acceptable water soluble polymer selected from the group of hydroxypropyl methylcellulose, hydroxypropyl cellulose, xanthan gum and karaya gum, and at least one pharmaceutically acceptable water insoluble polymer mixture selected from the group consisting of ethylcellulose and at least one of carboxypolymethylene, hydroxypropyl methylcellulose phthalate and hydroxypropyl cellulose, said polymers in an amount of about 30% to 72% by weight of the core; b) the seal coating comprises a film coating selected from the group consisting of enteric and non-enteric materials and mixtures thereof; and c) the sugar coating comprises sugar and a loading dose of said drug contained in the core. Dunn in U.S. Pat. Nos. 4,522,804, 4,521,402 and 4,521,401 describes constant order release solid oral. dosage formulations comprising an active ingredient, from about 0.5 to 6.0% of an acid-retardant or hydrophobic cellulose derivative, from about 2.5 to 35% of a hydrogenated vegetable oil, from about 1 to 20% of carbopol, from about 0.5 to 4.0% of fumed silicon dioxide and from about 0.4 to 3.0% of a lubricant.

Conventional hydrogels such as those based on high viscosity hydroxypropyl methylcelluloses are known to deliver medicaments at a constant rate independent of pH in relation to the hydration, gel viscosity and relative permeability of the dosage form. This, however, does not ensure that a drug whose solubility varies significantly as a function of pH will be delivered at a constant rate throughout the gastrointestinal pH range. With these conventional hydrogel formulations, the rate of drug release will be directly related to the solubility of the drug. If the drug possesses greater solubility in gastric fluids as compared to intestinal fluids, a characteristic of many weakly basic active ingredients, one would expect the release rate of the matrix to be faster in gastric fluids, than when the formulation makes the transition into the small intestine where the pH values are reported to be higher. For these formulations, if the dosage form is not retained for an adequate time period in the stomach, the decrease in drug release rate encountered in the intestine might result in incomplete bioavailability and greater variability from patient to patient.

Film coatings are known to have the ability to modify the release pattern of a drug once applied to pharmaceutical products. One type of film coating, known as an enteric coating, is used to prevent the release of drugs in, or protect drugs from, the effects of the gastric environment. Enteric coatings are used to delay the release of drugs which are inactivated by the stomach contents or which cause gastric irritation.

The matrix compositions of the present invention differ from existing formulations in that the present compositions have been designed to respond to increases in pH with a corresponding increase in the permeability of the dosage form. This allows the dosage form to release the active ingredient at an appropriate rate throughout the gastrointestinal tract.

SUMMARY OF THE INVENTION

This invention provides a matrix composition comprised of an active agent, a hydrophilic polymer, and an enteric polymer which results in a dosage form which is responsive to physiological pH changes. More specifically, the present invention relates to a sustained release matrix formulation in tablet unit dosage form comprising from about 0.1% by weight to about 90% by weight of an active agent, from about 5% by weight to about 29% by weight of a hydrophilic polymer, and from about 0.5% by weight to about 25% by weight of an enteric polymer, with the proviso that the total weight of the hydrophilic polymer and enteric polymer is less than 30% by weight of the formulation. This formulation reacts to an increase in pH with a corresponding increase in its permeability and rate of erosion. This results in an improved mechanism for the sustained delivery of a variety of compounds, especially those whose solubility declines as the pH is increased.

DETAILED DESCRIPTION OF THE INVENTION

Amounts and percentages are described herein as weight units unless otherwise stated.

The present formulation is in the form of a matrix of the ingredients comprising the formulation. A matrix, as defined herein, means a well-mixed composite of ingredients fixed into shape by tabletting. This intimate admixture of ingredients provides sustained release of the active agent contained therein as the pH of the environment changes following administration to a patient in need of such prolonged payout.

The percent of the ingredients required in the formulation of the invention, namely the active ingredient, the hydrophilic polymer, and the enteric polymer, is calculated on a dry weight basis without reference to any water or other components present. Thus, these three components together constitute 100 percent of the formulation for purposes of calculating individual percentages. If other ingredients are present, the sum of all of the components, with the exception of the filmcoating, if any, consitutes 100 percent of the formulation for purposes of calculating individual percentages.

The active ingredient will be any compound which is suitable for oral administration, although this invention is particularly advantageous for weakly basic agents. The active agent will be present in a composition of the invention at a concentration in the range of about 0.1% by weight to about 90% by weight, more preferably at a concentration in the range of about 45% by weight to about 85% by weight. Typical medicaments which might benefit from this type of delivery system are exemplified by, but not limited to, the following classes of agents: beta-blockers such as propranolol, metoprolol, atenolol, labetolol, timolol and pindolol; antimicrobial agents such as cephalexin, cefaclor, cefadroxil, cefuroxime, cefuroxime axetil, erythromycin, penicillin, 7-[D-(aminophenylacetyl)amino]-3-chloro-8-oxo-1-azabicyclo[4.2.0]oct-2-ene-2-carboxylic acid, also known as loracarbef, 7-[amino[3-[(methylsulfonyl)amino]-phenyl]acetyl]amino]amino]-3-chloro-8-oxo-1-azabicyclo[4.2.0]- oct-2-ene-2-carboxylic acid, and 7-[D-amino[3-[(ethylsulfonyl) amino]phenyl]acetyl-]amino-3-chloro-8-oxo-1-azabicyclo[4.2.0]oct-2-ene-2-carboxylic acid; antihypertensive agents such as clonidine, methyldopa and nifedipine; antihistamines such as chlorpheniramine and brompheniramine; tranquilizers such as diazepam, chlordiazepoxide and oxazepam; anticonvulsants; antinauseants; muscle relaxants; anti-inflammatory substances; psychotropics; antimanics; stimulants; decongestants; antianginal drugs; vasodilators; antiarrhythmics; vasoconstrictors; migraine treatments; antiemetics; diuretics; antispasmodics; antiasthmatics; anti-parkinson agents; expectorants; cough suppressants; mucolytics; vitamins; and mineral and nutritional additives.

Examples of agents for which this invention is particularly suited are cephalexin and cefaclor. Both compounds are zwitterions, possessing both an acidic and a basic functional group. Both have greater solubility at the low pH values reported for gastric fluids (pH 1-3), than at the values normally reported for intestinal fluids (pH 5-7). When these compounds are placed into a conventional hydrogel, the release rate will be faster in simulated gastric fluids than when the formulation is exposed to simulated intestinal fluids.

The compositions of the present invention will also contain a hydrophilic polymer. Hydrophilic polymers will be present in the compositions of the invention at a concentration in the range of about 5% by weight to about 29% by weight, more preferably from about 5% by weight to about 20% by weight. Hydrophilic polymers suitable for use in this invention are either water soluble or water swellable, and include one or more natural or partially or totally synthetic anionic or non-ionic hydrophilic gums, modified cellulosic substances or proteinaceous substances such as acacia, gum tragacanth, locust bean gum, guar gum, karaya gum, agar, pectin, carrageen, soluble and insoluble alginates, methylcellulose, hydroxypropyl methylcellulose, hydroxypropyl cellulose, hydroxyethylcellulose, sodium carboxymethylcellulose, carboxypolymethylene, gelatin, casein, zein, bentonite, magnesium aluminum silicate and the like. Other hydrophilic polymers which could be employed include polysaccharides and modified starch derivatives such as Amazio 721A (American Maize Products) and Pullulan (Hayashibara Biochemical Laboratories, Inc.).

Preferred hydrophilic polymers are the hydroxypropyl methylcelluloses manufactured by Dow Chemical and known as Methocel ethers. Preferred Methocel ethers include the Methocel E series gums (E 5, E 15, E 50, E4M, E10M and the like). The hydration rate of the Methocel E series gums is typically slower than the hydration rate of the Methocel K series gums. When the Methocel E series gums are used to prepare hydrogel tablets, thinner gel layers will result. As a consequence, when these tablets are exposed to a media of higher pH, the tablets respond more quickly than when polymers which provide thick viscous gel layers are employed. Yet another preferred polymer is Pullulan, a water soluble polysaccharide which is derived from starch. Pullulan is similar to the Methocel E series gums in that hydrogel tablets containing Pullulan normally form thin gel layers. When employed in conventional hydrogel tablets, Pullulan has only moderate ability to retard drug release.

The formulations of the invention will also contain an enteric polymer. These polymers will be present in the compositions of the invention at a concentration in the range of about 0.5% by weight to about 25% by weight, more preferably at a concentration in the range of about 1.5% by weight to about 15% by weight. The pH at which these polymers begin to dissolve will be in the range of about 5.0 to about 7.4. The polymers will be insoluble at a pH below about 5.0. Since these polymers are insoluble at the low pH values corresponding to gastric fluids, they aid in retarding drug release in these regions. When exposed to fluids of higher pH, similar to those found in the small intestine, these polymers will dissolve, and thereby increase the permeability and rate of erosion of tablets of the present invention. Examples of suitable polymers include acrylic resins such as Eudragit L, Eudragit S, Eudragit L-100-55- Rohm Pharma, acrylic latex dispersions, for example, Eudragit L30D- Rohm Pharma, as well as other polymers such as cellulose acetate phthalate, polyvinyl acetate phthalate, and hydroxypropyl methylcellulose phthalate. A preferred enteric polymer is Eudragit L-100-55. This resin is available both as a fine powder or as an aqueous dispersion Eudragit L30D. This resin begins to dissolve above a pH of about 5.5, and for this reason aids in improving drug release over a major portion of the small intestine. The total concentration of the hydrophilic polymer and the enteric polymer will be less than 30% by weight of the total formulation.

The present formulations may also contain a pharmaceutically acceptable binder at a concentration in the range of about 2.0% by weight to about 10.0% by weight, preferably from about 2.0% by weight to about 6.0% by weight. Pharmaceutically acceptable binders suitable for use in the present formulations are chosen from those routinely used by formulation chemists and include sucrose, lactose, gelatin, starch paste, acacia, tragacanth, and other gums; cellulose derivatives such as methylcellulose, sodium carboxymethylcellulose, hydroxypropyl cellulose, hydroxypropyl methylcellulose, and ethylcellulose; microcrystalline cellulose; povidone; polyethylene glycols; corn syrup; and other binders known to those familiar with pharmaceutical formulations. Preferred binders are Pullulan and hydroxypropyl cellulose.

The present formulations may also contain from about 2.0% to about 25.0% by weight of a pharmaceutically acceptable excipient, preferably from about 5% to 20% by weight. These excipients may be water soluble and should be chemically inert to the other ingredients. Preferable excipients would include lactose and mannitol. Alternatively, a variety of other known excipients could be employed such as glucose, fructose, xylose, galactose, sucrose, maltose, xylitol, sorbitol, as well as other pharmaceutically acceptable monosaccharides and disaccharides. Other suitable excipients world include inorganic compounds such as the chloride, sulfate and phosphate salts of potassium, sodium, and magnesium, as well as the calcium and succinate salts of citrate, phosphate, lactate and gluconate.

The present formulations may also contain a tablet lubricant. The lubricant will be present in the formulation at a concentration in the range of about 0.5% to about 4.0% by weight, preferably from about 1.0% to about 2.5% by weight. Preferred lubricants are stearic acid, in powder form, and magnesium stearate. Other suitable tablet lubricants are calcium or zinc stearate, hydrogenated vegetable oils, talc, polyethylene glycols, mineral oil or other pharmaceutically acceptable die wall lubricants.

If desired, other conventional tablet ingredients such as preservatives, stabilizers, glidants, pharmaceutically acceptable surface active agents, and FD&C colors may be included in the present formulations. The total weight of these ingredients is typically in the range of about 0.1% to about 2.0% of the weight of the formulation. Acceptable glidants or flow enhancers include colloidal silicon dioxide and talc. Acceptable surface active agents include sodium lauryl sulfate, dioctyl sodium sulfosuccinate (DSS), triethanolamine, polyoxyethylene sorbitan and poloxalkol derivatives, quaternary ammonium salts or other pharmaceutically acceptable surface active agents. Additionally, the lubricants and surface active agents can be combined and incorporated in the formulation as a single ingredient.

The resulting tablets may be coated, if desired, with one of many readily available coating systems. Coating the tablets serves to mask the taste of the drug, make the tablet easier to swallow and, in some cases, improve the appearance of the dosage form. The tablets can be sugar coated according to procedures well known in the art, or can be coated with any one of numerous polymeric film coating agents frequently employed by formulation chemists. Representative examples of such film coating agents include hydroxypropyl methylcellulose, carboxymethylcellulose, hydroxypropyl cellulose, methylcellulose, ethylcellulose, acrylic resins, povidone, polyvinyl diethylaminoacetate, cellulose acetate phthalate, polyvinyl acetate phthalate, hydroxypropyl methylcellulose phthalate, acrylic latex emulsions, ethylcellulose latex emulsions or other commercially available preparations such as Pharmacoat, manufactured by Shin-Etsu Chemical Co., Ltd, and Opadry, manufactured by Colorcon, Inc.

The present formulations may be prepared by procedures well known to formulation chemists. The method of manufacturing can affect the release characteristics of the finished tablets. The enteric polymer employed in the present formulations may be incorporated into the formulation in a number ways. The polymer may be added as a finely divided powder to the active agent along with all or part of the hydrophilic polymer. These ingredients are thoroughly mixed and granulated with either water or an aqueous solution of the hydrophilic polymer or other binder. This granulation is dried and sized. The resulting granulation may be blended with additional hydrophilic polymer and tablet lubricants, and then compressed into tablets. This particular method of manufacture requires a larger percentage of enteric polymer to yield the desired balance of appropriate release in both simulated gastric fluids and simulated intestinal fluids, but eliminates the need for organic solvents during the manufacture of the tablets.

Alternatively, the enteric polymer can be added as a finely divided powder to the active agent and optionally all or part of the hydrophilic polymer. These ingredients are thoroughly mixed. Next, rather than using aqueous ingredients during the granulation step, organic solvents such as isopropyl alcohol, ethanol and the like may be employed with or without water. If desired, a suitable hydrophilic polymer can be dissolved in the solvent. Using this type of granulating fluid, the finely divided enteric polymer may become activated or partially dissolved during the granulation phase. In this state, it may be more effective in retarding drug release at low pH. This granulation is then processed as described above. This method of incorporation may result in reduced requirements for both the enteric polymer and hydrophilic polymer, which may be a significant advantage when the active agent is very soluble or is to be employed at high doses.

A minor variation of the above method would be to dissolve the enteric polymer in an appropriate solvent system such as isopropyl alcohol, ethanol, and the like, with or without water. The resulting solution of the enteric polymer is then used to granulate the active agent which may optionally contain a portion of the hydrophilic polymer. This method of incorporation allows the enteric polymer to more effectively retard drug release at low pH. The resulting granulation is then processed as described above. This processing method may again result in reduced requirements for both the enteric polymer and hydrophilic polymer.

A third method for incorporation of the enteric polymer into a composition of the invention requires using an aqueous latex dispersion of the polymer as the granulating fluid. In this instance, the active agent and all or part of the hydrophilic polymer would be thoroughly mixed. The dispersion of the enteric polymer is then added to complete the granulation. The resulting tablets have many of the properties of the solvent granulation tablets described above, but this method does not require the use of these solvents. The aqueous dispersion, however, may not possess much tackiness, and the hydrophilic polymer which may be required to yield a suitable granulation by this method, may yield tablets which do not have the desired release profile at high and low pH that can be achieved using other manufacturing procedures.

The method of incorporation of the hydrophilic polymer will also have an effect on the release rate of the resulting tablets. These effects are well known to those familiar with hydrogel technology. It should be noted that when higher viscosity hydrophilic polymers are added to the formulation prior to wet granulation with aqueous solutions, the resulting tablets may have compromised release profiles when exposed to media of pH high enough to dissolve the enteric polymer.

As noted above, examples of agents for which this invention is particularly suited are cephalexin and cefaclor. When these compounds were placed into a conventional hydrogel composition, the release rate was faster in simulated gastric fluids than when the formulation was exposed to simulated intestinal fluids. This characteristic is demonstrated by the following example:

EXAMPLE A

The following example is a cephalexin monohydrate sustained release tablet prepared using conventional hydrogel technology:

| Per Tablet Unit Formula | weight (mg) |
|---|---|
| cephalexin | 1074.5 mg |
| povidone-90 | 24.0 mg |
| Methocel E4M Premium | 161.3 mg |
| stearic acid powder | 15.1 mg |
| magnesium stearate | 15.1 mg |

The release tendencies of these tablets were evaluated using two dissolution procedures. One procedure is termed the "gastric method" and the other procedure is the "simulated GI method". According to the gastric method, the tablets were evaluated in 0.1 N hydrochloric acid which represents simulated gastric fluids. The simulated gastrointestinal (GI) method was designed to simulate gastrointestinal transit. According to the simulated GI method, the tablets were exposed for one hour to 750 ml of 0.1 N hydrochloric acid, at which time the pH in the dissolution kettle was increased to pH 6.8 by the addition of 250 ml of 0.2 M tribasic sodium phosphate. The dissolution results of these tablets are presented below:

| | Cephalexin Dissolved (Cumulative Percent) | |
|---|---|---|
| Time (minutes) | Gastric Method | Simulated GI Method |
| 30 | 17 | 17 |
| 60 | 28 | 28 |
| 90 | 38 | 33 |
| 120 | 48 | 34 |
| 180 | 65 | 39 |
| 240 | 79 | 44 |
| 300 | 90 | 49 |
| 360 | 98 | 55 |
| 420 | 105 | 59 |

The tablets were placed into a 10 mesh basket and were rotated in the above media at 100 rpm.

The dissolution data illustrates a potential problem with the use of conventional hydrogel technology with a compound whose solubility declines as the pH is increased. With the above formulation, when the tablets were exposed to media of a higher pH in the simulated GI method, the release rate of cephalexin from the formulation declined dramatically. When used clinically, this formulation may not perform as intended if the dosage form does not remain in the stomach. Premature emptying of the tablet into the small intestine, and the resulting pH increase, could result in a decreased cephalexin release rate and poor bioavailability. These conditions would lead to potential problems if they occurred on a continued basis, such as therapeutic failure in the treatment of some types of infection.

The following Examples illustrate the formulations of the invention, and methods of for their preparation. The Examples are not intended to be limiting to the scope of the invention in any respect and should not be so construed.

EXAMPLE 1

A Hobart mixer was charged with 2149 g of cephalexin monohydrate. The resulting mixture was granulated with 1000 ml of 15% w/v Eudragit L-100-55 in a mixture of isopropyl alcohol:water (9:1, v:v). Total granulating time was between five to seven minutes. The wet granulation was placed through No. 4 screen onto paper-lined trays and dried at 35° C. for five and one-half hours. Drying was continued at room temperature overnight. The dried granulation was placed through a No. 14 mesh screen into an appropriate container.

A v-blender was charged with 575 g of this granulation and 62.5 g of hydroxypropyl methylcellulose E-50 to prepare 500 tablets. This mixture was blended for about thirty minutes. To the mixture was added stearic acid powder (7.5 g) and magnesium stearate (3.25 g) through a No. 30 mesh screen. This material was mixed for five minutes and discharged into an appropriate container. The resulting mixture was compressed on a Stokes F-press tabletting machine using conventional tooling.

| Per Tablet Unit Formula: | | |
|---|---|---|
| | weight (mg) | weight (percent) |
| cephalexin monohydrate | 1074.5 | 82.91 |
| Eudragit L-100-55 | 75.0 | 5.79 |
| hydroxypropyl methylcellulose E-50 | 125.0 | 9.65 |
| stearic acid powder | 15.0 | 1.15 |
| magnesium stearate | 6.5 | 0.50 |

The dissolution of these tablets was evaluated by the previously described methods with the following results:

| | Cephalexin Dissolved (Cumulative Percent) | |
|---|---|---|
| Time (minutes) | Gastric Method | Simulated GI Method |
| 30 | 22 | 20 |
| 60 | 35 | 32 |
| 90 | 45 | 40 |
| 120 | 53 | 50 |
| 180 | 66 | 69 |
| 240 | 77 | 84 |
| 300 | 85 | 92 |
| 360 | 94 | 93 |
| 420 | 100 | 93 |

EXAMPLE 2

A Hobart mixer was charged with 1612 g of cephalexin monohydrate, 300 g of Eudragit L-100-55 and 225 g of hydroxypropyl methylcellulose E-5 through an appropriate screen. The mixture was blended thoroughly and granulated with 750 ml of an 8% w/v hydroxypropyl methylcellulose E-5 solution in a mixture of isopropyl alcohol and water (3:7, v:v). Total granulating time was between five and ten minutes. The wet granulation was placed through a No. 4 screen onto paper-lined trays and dried at 45° C. for one half hour. Drying continued at room temperature for 48 hours. The dried granulation was placed through a No. 14 mesh screen into an appropriate container.

A v-blender was charged with 732 g of this granulation followed by 11 g of stearic acid powder and 7.77 g of magnesium stearate were added through a No. 30 mesh screen. This material was mixed for five minutes and discharged into an appropriate container. The resulting mixture was compressed on a Stokes F-press tabletting machine using conventional tooling.

The resulting tablets were film coated with a solvent based film coating mixture consisting of hydroxypropyl methylcellulose E-50 (1.581 weight percent) and glycerin (0.552 weight percent) in a conventional coating pan. The tablets were then placed onto paper-lined trays to dry to provide approximately 1000 tablets.

| Per Tablet Unit Formula: | weight (mg) | weight (percent) |
| --- | --- | --- |
| cephalexin monohydrate | 537.23 | 71.54 |
| Eudragit L-100-55 | 100.00 | 13.32 |
| hydroxypropyl methylcellulose E-5 | 95.00 | 12.65 |
| stearic acid powder | 11.00 | 1.46 |
| magnesium stearate | 7.77 | 1.03 |
| clear film coat (theory) | 15.88 | |

The dissolution of these tablets was evaluated by the previously described methods with the following results:

| Cephalexin Dissolved (Cumulative Percent) | | |
| --- | --- | --- |
| Time (minutes) | Gastric Method | Simulated GI Method |
| 30 | 28 | 27 |
| 60 | 48 | 46 |
| 90 | 65 | 60 |
| 120 | 82 | 73 |
| 180 | 100 | 93 |
| 240 | 100 | 99 |

EXAMPLE 3

A pony mixer was charged with 3224 g of cephalexin monohydrate, 300 g of Eudragit L-100-55 and 93 g of hydroxypropyl cellulose L.F. through an appropriate screen. The mixture was blended thoroughly and granulated with 1200 ml of a 6% w/v aqueous hydroxypropyl cellulose L.F. solution. Purified water was added in a quantity sufficient to produce a satisfactory granulation. Total granulating time was between five and ten minutes. The wet granulation was placed through a No. 4 screen onto paper-lined trays and dried at 35° C. for 20½ hours. The dried granulation was placed through a No. 12 mesh screen into an appropriate container.

To prepare 1000 tablets, a v-blender was charged with 1230 g of this granulation, and 100 g Methocel E4M CR grade was added through a No. 30 mesh screen. This mixture was blended for about 20 minutes, after which 15 g stearic acid powder and 10.5 g magnesium stearate were added through a No. 30 mesh screen. This material was mixed for five minutes and discharged into an appropriate container. The resulting mixture was compressed on a Stokes F-press tabletting machine using conventional tooling.

The resulting tablets were film coated with a solvent based film coating mixture consisting of hydroxypropyl methylcellulose E-50 (1.581 weight percent) and glycerin (0.552 weight percent) in a conventional coating pan. The tablets were placed onto paper-lined trays to dry.

| Per Tablet Unit Formula: | weight (mg) | weight (percent) |
| --- | --- | --- |
| cephalexin monohydrate | 1074.50 | 79.30 |
| Eudragit L-100-55 | 100.00 | 7.38 |
| hydroxypropyl cellulose L.F. | 55.00 | 4.06 |
| Methocel E4M CR grade | 100.00 | 7.38 |
| stearic acid powder | 15.00 | 1.11 |
| magnesium stearate | 10.50 | 0.77 |
| clear film coat (theory) | 50.54 | |

The dissolution of these tablets was evaluated by the previously described methods to provide the following results:

| Cephalexin Dissolved (Cumulative Percent) | | |
| --- | --- | --- |
| Time (minutes) | Gastric Method | Simulated GI Method |
| 30 | 12 | 12 |
| 60 | 31 | 30 |
| 90 | 47 | 37 |
| 120 | 60 | 41 |
| 180 | 80 | 58 |
| 240 | 93 | 72 |
| 300 | 99 | 82 |
| 360 | 103 | 89 |
| 420 | 105 | 93 |

EXAMPLE 4

A Hobart mixer was charged with 1612 g of cephalexin monohydrate and 45 g of hydroxypropyl cellulose L.F. through an appropriate screen. This mixture was blended thoroughly and granulated with 500 ml of an aqueous dispersion Eudragit L30D (equivalent to 150 g Eudragit L-100-55). Purified water was added in a quantity sufficient to produce a satisfactory granulation. Total granulating time was between five and ten minutes. The wet granulation was placed through a No. 4 screen onto paper-lined trays and dried at 35° C. for 20 hours. The dried granulation was placed through a No. 14 mesh screen into an appropriate container.

To prepare 500 tablets, a v-blender was charged with 602 g of this granulation and 50 g of Methocel E4M CR grade was added through a No. 30 mesh screen. This mixture was blended for about 20 minutes, after which 7.5 g of stearic acid powder and 5.25 g magnesium stearate were added through a No. 30 mesh screen. This material was mixed for five minutes and discharged into an appropriate container. The resulting mixture was compressed on a Stokes F-press tabletting machine using conventional tooling.

| Per Tablet Unit Formula: | weight (mg) | weight (percent) |
| --- | --- | --- |
| cephalexin monohydrate | 1074.50 | 80.79 |
| Eudragit L30D (solids) | 100.00 | 7.52 |
| hydroxypropyl cellulose L.F. | 30.00 | 2.26 |
| Methocel E4M CR grade | 100.00 | 7.52 |
| stearic acid powder | 15.00 | 1.13 |
| magnesium stearate | 10.50 | 0.78 |

The dissolution of these tablets was evaluated by the previously described methods to give the following results:

| Cephalexin Dissolved (Cumulative Percent) | | |
|---|---|---|
| Time (minutes) | Gastric Method | Simulated GI Method |
| 30 | 22 | 21 |
| 60 | 33 | 32 |
| 90 | 42 | 37 |
| 120 | 50 | 39 |
| 180 | 63 | 49 |
| 240 | 75 | 67 |
| 300 | 85 | 79 |
| 360 | 93 | 85 |
| 420 | 97 | 88 |

EXAMPLE 5

A Hobart mixer was charged with 2149 g of cephalexin monohydrate. This material was granulated with 1000 ml of a 10% w/v Eudragit L-100-55 in a mixture of isopropyl alcohol and water (9:1, v:v). Total granulating time was about seven minutes. The wet granulation was placed through a No. 4 screen onto paper-lined trays and dried at 35° C. for two hours. Drying was continued at room temperature overnight. The dried granulation was placed through a No. 14 mesh screen into an appropriate container.

To prepare 300 tablets, a v-blender was charged with 337 g of the granulation and 45 g of hydroxypropyl methylcellulose E-50. This mixture was blended for about thirty minutes. Stearic acid powder (4.5 g) and magnesium stearate (1.95 g) were added to the mixture through a No. 30 mesh screen. This material was mixed for five minutes and discharged into an appropriate container. The resulting mixture was compressed on a Stokes F-press tabletting machine using conventional tooling.

| Per Tablet Unit Formula: | | |
|---|---|---|
| | weight (mg) | weight (percent) |
| cephalexin monohydrate | 1074.5 | 82.91 |
| Eudragit L-100-55 | 50.0 | 3.86 |
| hydroxypropyl methylcellulose E-50 | 150.0 | 11.57 |
| stearic acid powder | 15.0 | 1.16 |
| magnesium stearate | 6.5 | 0.50 |

The dissolution of these tablets was evaluated by the previously described methods with the following results:

| Cephalexin Dissolved (Cumulative Percent) | | |
|---|---|---|
| Time (minutes) | Gastric Method | Simulated GI Method |
| 30 | 24 | 24 |
| 60 | 38 | 37 |
| 90 | 47 | 46 |
| 120 | 54 | 55 |
| 180 | 73 | 76 |
| 240 | 94 | 89 |
| 300 | 99 | 94 |

EXAMPLE 6

A Hobart mixer was charged with 500 g of cefaclor monohydrate, 65 g of lactose and 100 g of hydroxypropyl methylcellulose E-5 through an appropriate screen. The mixture was blended thoroughly and granulated with 350 ml of a 5% w/v Eudragit L-100-55 solution in a mixture of isopropyl alcohol and water (19:1, v:v). Total granulating time was between five and ten minutes. The wet granulation was placed through a No. 4 screen onto paper-lined trays and dried at 50° C. for one hour. Drying continued at room temperature for 48 hours. The dried granulation was passed through a No. 16 mesh screen into an appropriate container.

To prepare 500 tablets, a v-blender was charged with 268 g of the granulation, and 3.75 g of stearic acid powder and 2.5 g of magnesium stearate were added through a No. 30 mesh screen. The resulting mixture was mixed for five minutes and discharged into an appropriate container. The resulting mixture was compressed on a Stokes F-press tabletting machine using conventional tooling.

| Per Tablet Unit Formula: | | |
|---|---|---|
| | weight (mg) | weight (percent) |
| cefaclor monohydrate | 392.30 | 71.60 |
| lactose | 50.98 | 9.30 |
| Eudragit L-100-55 | 13.71 | 2.50 |
| hydroxypropyl methylcellulose E-5 | 78.45 | 14.32 |
| stearic acid powder | 7.50 | 1.37 |
| magnesium stearate | 5.00 | 0.91 |

The dissolution of these tablets was evaluated by the previously described methods with the following

| Cefaclor Dissolved (Cumulative Percent) | | |
|---|---|---|
| Time (minutes) | Gastric Method | Stimulated GI Method |
| 30 | 22 | 23 |
| 60 | 33 | 32 |
| 90 | 41 | 54 |
| 120 | 47 | 97 |
| 180 | 61 | 112 |
| 240 | 75 | |
| 300 | 85 | |
| 360 | 92 | |
| 420 | 97 | |

EXAMPLE 7

A Hobart mixer was charged with 500 g of cefaclor monohydrate, 40 g of Eudragit L-100-55, 50 g of lactose and 75 g of Pullulan PI-20 through an appropriate screen. The mixture was blended thoroughly and granulated with 200 ml of a 5% w/v hydroxypropyl cellulose L.F. solution in a mixture of isopropyl alcohol and water (19:1, v:v). Total granulating time was between five and ten minutes. The wet granulation was placed through a No. 4 screen onto paper-lined trays and then dried at 50° C. for two hours. Drying continued at room temperature for 24 hours. The dried granulation was placed through a No. 14 mesh screen into an appropriate container.

A v-blender was charged with 266 g of the granulation, and 3.75 g stearic acid powder and 2.5 g of magnesium stearate were added to the blender through a No. 30 mesh screen. This material was mixed for five minutes and discharged into an appropriate container. The resulting mixture was compressed on a Stokes F-press tabletting machine using conventional tooling to provide 500 tablets.

| Per Tablet Unit Formula: | | |
|---|---|---|
| | weight (mg) | weight (percent) |
| cefaclor monohydrate | 392.30 | 73.43 |
| lactose | 39.23 | 7.34 |
| Eudragit L-100-55 | 31.36 | 5.87 |
| Pullulan PI-20 | 58.85 | 11.02 |
| stearic acid powder | 7.50 | 1.40 |
| magnesium stearate | 5.00 | 0.94 |

The dissolution of these tablets was evaluated by the previously described methods to afford the following results:

| Cefaclor Dissolved (Cumulative Percent) | |
|---|---|
| Time (minutes) | Gastric Method |
| 30 | 18 |
| 60 | 24 |
| 90 | 30 |
| 120 | 34 |
| 180 | 44 |
| 240 | 50 |
| 300 | 56 |
| 360 | 61 |
| 420 | 66 |

EXAMPLE 8

A Hobart mixer was charged with 1177 g of cefaclor monohydrate, 212 g of mannitol and 176 g of hydroxypropyl methylcellulose E-5 through an appropriate screen. The mixture was blended thoroughly and granulated with 720 ml of a 5% w/v Eudragit L-100-55 solution in a mixture of isopropyl alcohol and water (9:1, v:v). Total granulating time was five minutes. The wet granulation was placed through a No. 4 screen onto paper-lined trays and dried at 40° C. for three hours. Drying continued at room temperature overnight. The dried granulation was placed through a No. 16 mesh screen into an appropriate container.

To prepare 1500 tablets, a v-blender was charged with 800 g of this granulation. Stearic acid powder (11.25 g) and magnesium stearate (7.5 g) were added to the blender through a No. 30 mesh screen. The resulting material was mixed for five minutes and discharged into an appropriate container. The resulting mixture was compressed on a Stokes F-press tabletting machine using conventional tooling.

| Per Tablet Unit Formula: | | |
|---|---|---|
| | mg/tablet | % w/w |
| cefaclor monohydrate | 392.30 | 71.83 |
| mannitol | 70.70 | 12.95 |
| hydroxypropyl methylcellulose E-5 | 58.50 | 10.71 |
| Eudragit L-100-55 | 12.00 | 2.20 |
| stearic acid powder | 7.50 | 1.37 |
| magnesium stearate | 5.00 | 0.94 |

The dissolution of these tablets was evaluated by the previously described methods with the following results:

| Cefaclor Dissolved (Cumulative Percent) | | |
|---|---|---|
| Time (minutes) | Gastric Method | Simulated GI Method |
| 30 | 20 | 21 |
| 60 | 31 | 30 |
| 90 | 38 | 61 |
| 120 | 46 | 111 |
| 180 | 63 | |
| 240 | 79 | |
| 300 | 91 | |
| 360 | 98 | |
| 420 | 103 | |

EXAMPLE 9

A Hobart mixer was charged with 1177 g of cefaclor monohydrate, 212 g of mannitol and 176 g of hydroxypropyl methylcellulose E-5 through an appropriate screen. The mixture was blended thoroughly and then granulated with 720 ml of a 5% w/v Eudragit L-100-55 solution in a mixture of isopropyl alcohol and water (9:1, v:v). Total granulating time was about five minutes. The wet granulation was placed through a No. 4 screen onto paper-lined trays and dried at 40° C. for three hours. Drying continued at room temperature overnight. The dried granulation was placed through a No. 16 mesh screen into an appropriate container.

To prepare 1100 tablets, a v-blender was charged with 587 g of this granulation and 26.4 g of mannitol. This mixture was blended for about thirty minutes and combined with stearic acid powder (8.25 g) and magnesium stearate (5.5 g) through a No. 30 mesh screen. This material was mixed for five minutes and discharged into an appropriate container. The resulting mixture was compressed on a Stokes F-press tabletting machine using conventional tooling. The resulting tablets were film coated with a solvent based film coating mixture consisting of hydroxypropyl methylcellulose E-50 (1.55 weight percent), glycerin (0.54 weight percent) and Opaspray Blue (solids - 0.75 weight percent) in a conventional coating pan. The tablets were then placed onto paper-lined trays to dry.

| Per Tablet Unit Formula: | | |
|---|---|---|
| | weight (mg) | weight (percent) |
| cefaclor monohydrate | 392.30 | 68.82 |
| mannitol | 94.70 | 16.61 |
| hydroxypropyl methylcellulose E-5 | 58.50 | 10.26 |
| Eudragit L-100-55 | 12.00 | 2.11 |
| stearic acid powder | 7.50 | 1.32 |
| magnesium stearate | 5.00 | 0.88 |
| color film coating (theory) | 13.01 | |

The dissolution of these tablets was evaluated by the previously described methods with the following results:

| Cefaclor Dissolved (Cumulative Percent) | | |
|---|---|---|
| Time (minutes) | Gastric Method | Simulated GI Method |
| 30 | 18 | 18 |
| 60 | 28 | 28 |
| 90 | 36 | 53 |
| 120 | 46 | 95 |
| 180 | 66 | |
| 240 | 83 | |
| 300 | 93 | |

-continued

| Time (minutes) | Cefaclor Dissolved (Cumulative Percent) | |
|---|---|---|
| | Gastric Method | Simulated GI Method |
| 360 | 97 | |

EXAMPLE 10

A Hobart mixer was charged with 1569 g o cefaclor monohydrate, 201 g of mannitol and 264 g of hydroxypropyl methylcellulose E-5 through an appropriate screen. The mixture was blended thoroughly and granulated with 960 ml of a 5% w/v Eudragit L-100-55 solution in a mixture of isopropyl alcohol and water (9:1, v:v). Total granulating time was about six minutes. The wet granulation was placed through a No. 4 screen onto paper-lined trays and dried at 28° C. for six hours. Drying continued at room temperature overnight. The dried granulation was passed through a No. 16 mesh screen into an appropriate container.

To prepare 1500 tablets, a v-blender was charged with 781 g of the granulation, 11.25 g of stearic acid powder and 7.5 g of magnesium stearate. The lubricants were added through a No. 30 mesh screen. This material was mixed for five minutes and discharged into an appropriate container. The resulting mixture was then compressed on a Stokes F-press tabletting machine using conventional tooling. The resulting tablets were film coated with a solvent based film coating mixture consisting of hydroxypropyl methylcellulose E-50 (1.55 weight percent), glycerin (0.54 weight percent) and Opaspray Blue (solids—0.75 weight percent) in a conventional coating pan. The tablets were then placed onto paper-lined trays to dry.

| Per Tablet Unit Formula: | | |
|---|---|---|
| | weight (mg) | weight (percent) |
| cefaclor monohydrate | 392.30 | 73.60 |
| mannitol | 50.20 | 9.42 |
| hydroxypropyl methylcellulose E-5 | 66.00 | 12.38 |
| Eudragit L-100-55 | 12.00 | 2.25 |
| stearic acid powder | 7.50 | 1.41 |
| magnesium stearate | 5.00 | 0.94 |
| color film coating (theory) | 12.87 | |

The dissolution of these tablets was evaluated by the previously described methods with the following results:

| Time (minutes) | Cefaclor Dissolved (Cumulative Percent) | |
|---|---|---|
| | Gastric Method | Simulated GI Method |
| 30 | 17 | 17 |
| 60 | 26 | 26 |
| 90 | 33 | 45 |
| 120 | 38 | 82 |
| 180 | 49 | |
| 240 | 58 | |
| 300 | 67 | |
| 360 | 76 | |
| 420 | 83 | |

EXAMPLE 11

A Hobart mixer was charged with 1046 g of cefaclor monohydrate, 80 g of mannitol and 70 g of hydroxypropyl methylcellulose E-5 through an appropriate screen. The mixture was blended thoroughly and then granulated with 500 ml of a 3% w/v Eudragit L-100-55 w/v hydroxypropyl cellulose EF solution in a mixture of isopropyl alcohol and water (isopropyl alcohol 90 parts : 10 parts water). Total granulating time was between three and four minutes. The wet granulation was placed through a No. 4 screen onto paper-lined trays and then dried at 40° C. for five hours. Drying continued at room temperature for 24 hours. The dried granulation was placed through a No. 16 mesh screen and the granulation was returned to paper-lined trays and dried at 40° C. for 2½ hours to remove residual solvent.

To prepare 900 tablets, a v-blender was charged with 550.8 g of this granulation. To this, 61.2 g of hydroxypropyl methylcellulose E-50 was added through a No. 30 mesh screen. The mixture was blended for twenty minutes in a v-blender. To this mixture, the lubricants stearic acid powder (6.3 g) and magnesium stearate (2.7 g) were added through a No. 30 mesh screen. This material was mixed for five minutes and discharged into an appropriate container. The resulting mixture was then compressed on a Stokes F-press tableting machine using conventional tooling.

The tablets were film coated with a solvent based film coating mixture consisting of hydroxypropyl methylcellulose E-50 (1.581 weight percent), glycerin 0.552 (weight percent) and Opaspray Blue (1.961 weight percent) in a conventional coating pan. The tablets were placed onto paper-lined trays to air dry.

| Per Tablet Unit Formula: | | |
|---|---|---|
| | weight (mg) | weight (percent) |
| cefaclor monohydrate | 523.00 | 75.80 |
| mannitol | 40.20 | 5.80 |
| hydroxypropyl methylcellulose E-5 | 35.00 | 5.07 |
| Eudragit L-100-55 | 7.50 | 1.09 |
| hydroxypropyl cellulose EF | 6.50 | 0.94 |
| hydroxypropyl methylcellulose E-50 | 68.00 | 9.86 |
| stearic acid powder | 7.00 | 1.01 |
| magnesium stearate | 3.00 | 0.43 |
| blue film coating (theory) | 12.50 | |

The dissolution of these tablets was evaluated by the previously described methods with the following results:

| Time (minutes) | Cefaclor Dissolved (Cumulative Percent) | |
|---|---|---|
| | Gastric Method | Simulated GI Method |
| 30 | 16 | 17 |
| 60 | 30 | 34 |
| 90 | 44 | 56 |
| 120 | 57 | 71 |
| 180 | 81 | 88 |
| 240 | 101 | 100 |

EXAMPLE 12

To prepare 40 tablets, the following ingredients were passed through a No. 30 mesh screen and mixed together in a mortar and pestle- 8.44 g of 7- [D-(aminophenylacetyl)amino]-3-chloro-8-oxo-1-azabicyclo[4.2.0]oct-2-ene-2-carboxylic acid monohydrate, 0.84 g of Eudragit L-100-55, and 2.56 g of hydroxypropyl methylcellulose E-50. To this mixture, 0.104 g of magnesium stearate and 0.216 g of talc were added and blended thoroughly. The resulting mixture was then compressed on a Stokes F-press tableting machine using conventional tooling.

Per Tablet Unit Formula:

| | weight (mg) | weight (percent) |
|---|---|---|
| 7-[D-(aminophenylacetyl)amino]-3-chloro-8-oxo-1-azabicyclo-[4.2.0]oct-2-ene-2-carboxylic acid monohydrate | 211.00 | 69.41 |
| Eudragit L-100-55 | 21.00 | 6.91 |
| hydroxypropyl methylcellulose E-50 | 64.00 | 21.05 |
| magnesium stearate | 2.60 | 0.86 |
| talc | 5.40 | 1.78 |

The dissolution of these tablets was evaluated by the previously described methods with the following results:

Active Agent Dissolved (Cumulative Percent)

| Time (minutes) | Gastric Method | Simulated GI Method |
|---|---|---|
| 30 | 23 | 24 |
| 60 | 43 | 44 |
| 90 | 65 | 59 |
| 120 | 80 | 68 |
| 150 | 92 | 79 |
| 180 | 100 | 87 |
| 240 | 105 | 99 |
| 300 | 104 | 105 |

EXAMPLE 13

To prepare 40 tablets, the following ingredients were passed through a No. 30 mesh screen and mixed together in a mortar and pestle- 8.0 g of 7-[[amino [3-[(methylsulfonyl)amino]phenyl]acetyl]amino]-3-chloro-8-oxo-1-azabicyclo[4.2.0]oct-2-ene-2-carboxylic acid, 0.8 g of Eudragit L-100-55, 1.6 g of hydroxypropyl methylcellulose E-50, and 0.96 g of Methocel E4M CR grade. To this mixture, 0.120 g of magnesium stearate and 0.200 g of talc were added and blended thoroughly. The resulting mixture was then compressed on a Stokes F-press tableting machine using conventional tooling.

Per Tablet Unit Formula:

| | weight (mg) | weight (percent) |
|---|---|---|
| 7-[[amino-[3-[(methylsulfonyl)-amino]phenyl]acetyl]amino]-3-chloro-8-oxo-1-azabicyclo[4.2.0]-oct-2-ene-2-carboxylic acid | 200.00 | 68.49 |
| Eudragit L-100-55 | 20.00 | 6.85 |
| hydroxypropyl Methylcellulose E-50 | 40.00 | 13.70 |
| Methocel E4M CR grade | 24.00 | 8.22 |
| magnesium stearate | 3.00 | 1.03 |
| talc | 5.00 | 1.71 |

The dissolution of these tablets was evaluated by the previously described methods with the following results:

Active Agent Dissolved (Cumulative Percent)

| Time (minutes) | Gastric Method | Simulated GI Method |
|---|---|---|
| 30 | 19 | 18 |
| 60 | 29 | 28 |
| 90 | 40 | 36 |
| 120 | 50 | 40 |
| 150 | 58 | 43 |
| 180 | 65 | 48 |
| 240 | 78 | 58 |
| 300 | 89 | 69 |
| 360 | 97 | 78 |
| 420 | 100 | 84 |

EXAMPLE 14

To prepare 40 tablets, the following ingredients were passed through a No. 30 mesh screen and mixed together in a mortar and pestle- 8.0 g of 7- D-[amino[3-[(ethyl-sulfonyl)amino]phenyl]acetyl]amino]- -chloro-8-oxo-1-azabicyclo[4.2.0]oct-2-ene-2-carboxylic acid, 0.8 g of Eudragit L-100-55, 1.6 g of hydroxypropyl methylcellulose E-50, and 1.0 g of Methocel E4M CR grade. To this mixture, 0.20 g of magnesium stearate and 0.200 g of talc were added and blended thoroughly. The resulting mixture was then compressed on a Stokes F-press tableting machine using conventional tooling.

Per Tablet Unit Formula:

| | weight (mg) | weight (percent) |
|---|---|---|
| 7-[D-[amino[3-[(ethylsulfonyl)-amino]phenyl]acetyl]amino]-3-chloro-8-oxo-1-azabicyclo[4.2.0]-oct-2-ene-2-carboxylic acid | 200.00 | 67.80 |
| Eudragit L-100-55 | 20.00 | 6.78 |
| hydroxypropyl methylcellulose E-50 | 40.00 | 13.56 |
| Methocel E4M CR grade | 25.00 | 8.47 |
| magnesium stearate | 5.00 | 1.69 |
| talc | 5.00 | 1.69 |

The dissolution of these tablets was evaluated by the previously described methods with the following results:

Active Agent Dissolved (Cumulative Percent)

| Time (minutes) | Gastric Method | Simulated GI Method |
|---|---|---|
| 30 | 18 | 17 |
| 60 | 27 | 28 |
| 90 | 34 | 35 |
| 120 | 43 | 39 |
| 150 | 50 | 42 |
| 180 | 56 | 47 |
| 240 | 67 | 56 |
| 300 | 76 | 65 |
| 360 | 86 | 75 |
| 420 | 92 | 84 |

We claim:

1. A sustained release matrix formulation in tablet unit dosage from comprising from about 0.1% by weight to about 90% by weight of cefaclor, from about 5% by weight to about 29% by weight of a hydrophilic polymer, and from about 0.5% by weight to about 25% by weight of an acrylic polymer which dissolves at a pH in the range of about 5.0 to about 7.4, with the proviso that the total weight of the hydrophilic polymer and said acrylic polymer is less than 30% by weight of the formulation.

2. A formulation of claim 1 wherein the cefaclor is present at a concentration in the range of about 45% by weight to about 85% by weight.

3. A formulation of claim 1 wherein the hydrophilic polymer is present at a concentration in the range of about 5% by weight to about 20% by weight.

4. A formulation of claim 1 wherein the acrylic polymer is present at a concentration in the range of about 1.5% by weight to about 15% by weight.

5. The formulation of claim 1 which consists essentially of the following ingredients, in percent by weight:

| Ingredient | Weight (Percent) |
| --- | --- |
| Cefaclor | 75.80 |
| mannitol | 5.80 |
| hydroxypropyl methylcellulose | 14.93 |
| methacrylic acid copolymer | 1.09 |
| hydroxypropyl cellulose | 0.94 |
| stearic acid powder | 1.01 |
| magnesium stearate | 0.43 |

* * * * *

UNITED STATES PATENT AND TRADEMARK OFFICE
CERTIFICATE OF CORRECTION

PATENT NO. : 4,968,508

DATED : November 6, 1990

INVENTOR(S) : Peter L. Oren et al.

It is certifed that an error apears in the above-identified patent and that said Letters Patent is hereby corrected as shown below:

Column 3, line 28, "7-[amino" should read -- 7-[[amino -- .

Column 3, line 29, "amino]amino]-3-chloro" should read -- amino]-3-chloro -- .

Column 3, line 31, "[D-amino" should read -- [D-[amino -- .

Column 12, line 29, after the word "following" insert -- results: -- .

Column 15, line 10, "1569 g o" should read -- 1569 g of -- .

Column 16, line 2, following "Eudragit L-100-55" insert -- and 2.6% --.

Column 18, line 17, "7-D-[amino" should read -- 7-[D-[amino --.

Column 18, line 18, "acetyl]amino]- -chloro-" should read -- acetyl]amino]-3-chloro- -- .

UNITED STATES PATENT AND TRADEMARK OFFICE
CERTIFICATE OF CORRECTION

PATENT NO. : 4,968,508
DATED : November 6, 1990
INVENTOR(S) : Peter L. Oren, et. al.

It is certified that error appears in the above-indentified patent and that said Letters Patent is hereby corrected as shown below:

Column 18, line 60, "dosage from" should read -- dosage form--.

Signed and Sealed this

Twenty-eighth Day of September, 1993

Attest:

BRUCE LEHMAN

Attesting Officer     Commissioner of Patents and Trademarks